United States Patent [19]
Tankovich

[11] Patent Number: 5,165,418
[45] Date of Patent: Nov. 24, 1992

[54] BLOOD SAMPLING DEVICE AND METHOD USING A LASER

[76] Inventor: Nikola I. Tankovich, 8925 Helen James Ave., San Diego, Calif. 92126

[21] Appl. No.: 844,786

[22] Filed: Mar. 2, 1992

[51] Int. Cl.$^5$ ............................................... A61B 5/00
[52] U.S. Cl. ........................................ 128/760; 606/16
[58] Field of Search ............... 128/760, 763, 770, 771; 606/13–17, 2, 3, 9, 109, 181, 185

[56] References Cited

U.S. PATENT DOCUMENTS

| | | | |
|---|---|---|---|
| 4,712,537 | 12/1987 | Pender | 606/109 |
| 4,949,728 | 8/1990 | Brook | 128/760 |
| 5,102,410 | 4/1992 | Dressel | 606/17 |

*Primary Examiner*—Max Hindenburg
*Attorney, Agent, or Firm*—John R. Ross

[57] ABSTRACT

A laser and method for punching tiny holes in human skin for the purpose of taking blood samples. A laser is provided for producing laser pulses in a narrow beam having a cross section of about 0.2 to 1.5 millimeter in diameter to deposit 0.5 joules to 4 joules of laser energy on the skin in a time period of between 5 us and 600 us. A preferred method comprises directing a 1.5 joule, 150 us, 0.5 millimeter diameter pulse at a patient's finger tip. The pulse vaporizes a hole about 1 mm in diameter and 1.5 mm deep to produce about one to three drops of blood for a blood sample. In another preferred embodiment a large vein in the arm is punctured by a four pulse beam of 1.5 joule pulses. A hole of about 1 mm diameter and about 4 mm deep is produced which permits blood samples of several milliliters to be taken.

7 Claims, 2 Drawing Sheets

BLOOD SAMPLING DEVICE AND METHOD USING A LASER

BACKGROUND OF THE INVENTION

The taking of blood samples is a very important part of the process of diagnosing and controlling disease. The traditional method used for taking small blood samples for blood formula and glucose measurement is to puncture the skin of a finger with a sharp object like a needle or pointed blade. For the taking of larger samples for other blood analysis a vein is usually punctured with a syringe needle. These methods are almost always painful and frightening, especially for children. In addition there is growing concern regarding the possibility of contracting AIDS by a contaminated needle or blade.

What is needed is a simple method and device for taking blood samples which virtually eliminates pain, stress and any risk of infection.

SUMMARY OF THE INVENTION

The present invention provides a laser and method for punching tiny holes in human skin for the purpose of taking blood samples. A laser is provided for producing laser pulses in a narrow beam having a cross section of about 0.2 to 1.5 millimeter in diameter to deposite 0.5 joules to 4 joules of laser energy on the skin in a time period of between 5 us and 600 us. A preferred method comprises directing a 1.5 joule, 150 us, 0.5 millimeter diameter pulse at a patient's finger tip. The pulse vaporizes a hole about 1 mm in diameter and 1.5 mm deep to produce about one to three drops of blood for a blood sample. In another preferred embodiment a large vein in the arm is punctured by a four pulse beam of 1.5 joule pulses. A hole of about 1 mm diameter and about 4 mm deep is produced which permits blood samples of several milliliters to be taken.

DETAILED DESCRIPTION OF PREFERRED EMBODIMENTS

The present invention can be described by reference to the figures.

Small Samples

The simplist embodiment of the present invention is a Erbrium laser calibrated to produce single pulse having durations of about 150 us and between about 1.5 Joules per pulse.

Figure 1:
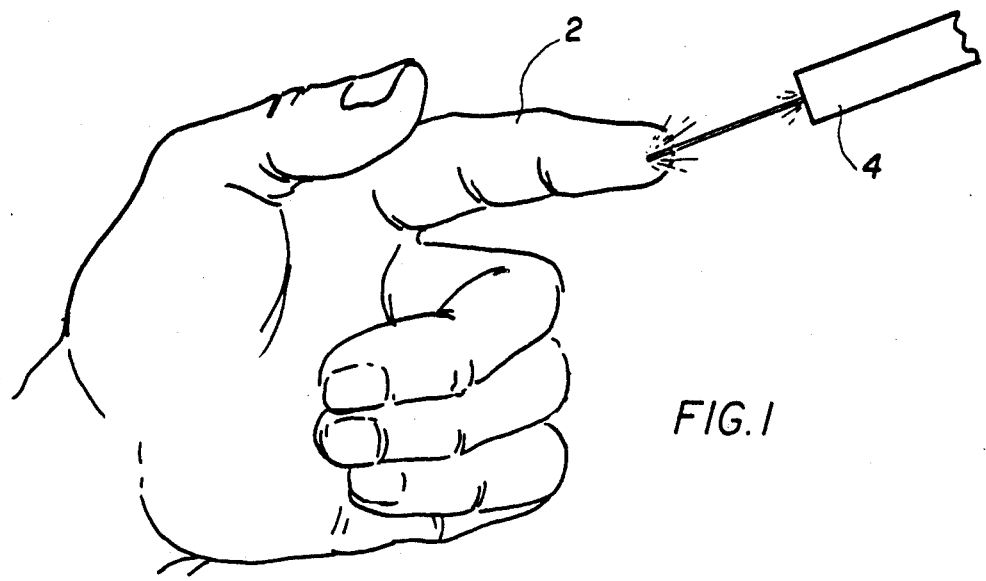
FIG. 1 shows a finger being punctured by an Erbrium laser.

As shown in FIG. 1 a patient's finger 2 is irradiated with a single pulse of 150 us duration from an Erbrium laser and the pulse is focused on a skin area of having a diameter of about 0.5 mm to 1.0 mm. The wavelength of the Erbrium laser beam is 2.94 microns and at this wavelength the large majority of the energy is absorbed in human skin tissue. The absorption of the laser energy applied in a very short high power pulse 5 results in the energy being dissipated by vaporizing the skin tissue. The depth of the hole is determined by the energy of the pulse.

Thus, the depth of tissue removed roughly equals the incident energy density (joules per square millimeter) multiplied by the ablation efficiency (540 ug/Joule) and divided by the density of skin (about 1 g/cubic cm. Thus, with a 1.5 joule Erbrium laser pulse on 0.5 mm diameter spot a vaporized hole in the skin of about 0.5 mm wide and 3.8 mm deep would be predicted:

$$\text{Depth of Hole} = \frac{\frac{1.5 \text{ joules}}{(3.14 \times .25 \text{ mm} \times .25 \text{ mm})} \quad 540 \text{ ug/Joule}}{1{,}000 \text{ ug/cubic mm}}$$

$$= 4 \text{ mm}$$

Actual depth of the hole is a little wider (about 1 mm) and about one half of this estimated depth or about 1.5 mm.

Figure 2:
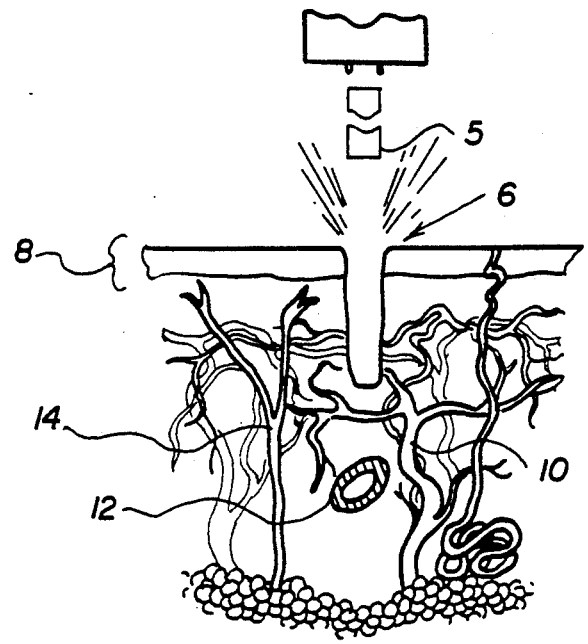
FIG. 2 shows a skin cross section and the hole made by the laser pulse for a small blood sample.

FIG. 2 is a sketch of a layer of skin in the finger. One square inch of skin contains up to 15 feet of blood vessels as indicated by 10 and 12 in FIG. 2. On the finger the vessels are within about 0.1 mm of the skin surface so that the hole described above, 6 in FIG. 2, will sever many small vessels 10 and 12. However, as indicated in FIG. 2 nerve endings with sensorsy corpuscle 14 are typically no closer than about 2½ mm from the skin surface. Thus, a blood sample can normally be taken with no significant sensation of pain. In actual practice some pain may be experienced although when there is pain, it typically much less than the pain experienced with a puncture procedure. The bleeding from this 0.5 mm to 1 mm diameter hole will typically stop after about one to three drops has escaped. A little pressure will speed the clotting. Deeper holes can be obtained by increasing the energy of the pulse or by applying several pulses adding up to greater energy but within a short timeframe of about 100 to 300 us.

Large Sample

Figure 3:
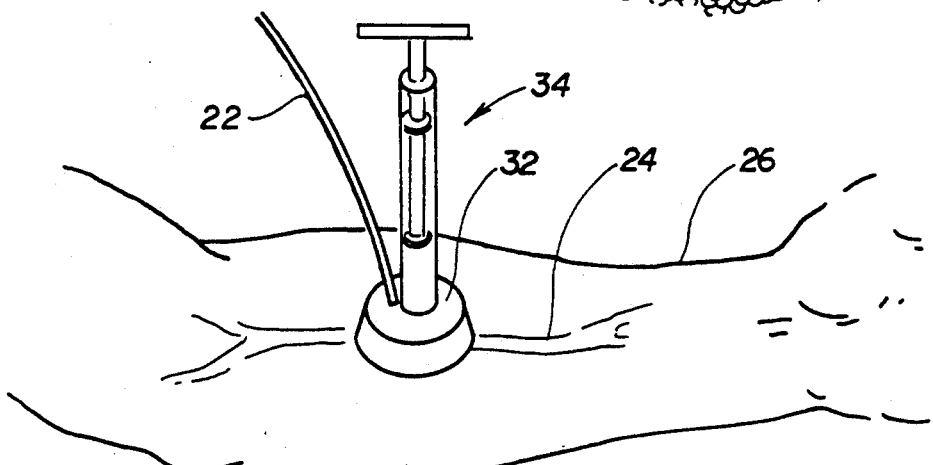
FIG. 3 shows a surface arm vein being punctured by a pulsed laser beam and a large sample is removed using a syringe with a silicon rubber tip.

A second preferred embodiment of the present invention can be described by reference to FIG. 3. In this case a laser beam is guided through fiber optic 22 to a large surface vein 24 on a patient's arm 26. In this case four 1.5 Joule pulses vaporize a 2 to 5 mm deep hole with a diameter of about 1.0 to 1.5 mm through the patient's skin and the top of vein 24. When the laser penetrates the large vein, blood begins to flow out of the skin because of the blood pressure. Silicon rubber suction pad 32 maintains a seal to allow syringe device 34 to provide a vacuum. Syringe device 34 is used to suck several grams of blood from vein 24.

Figure 4:
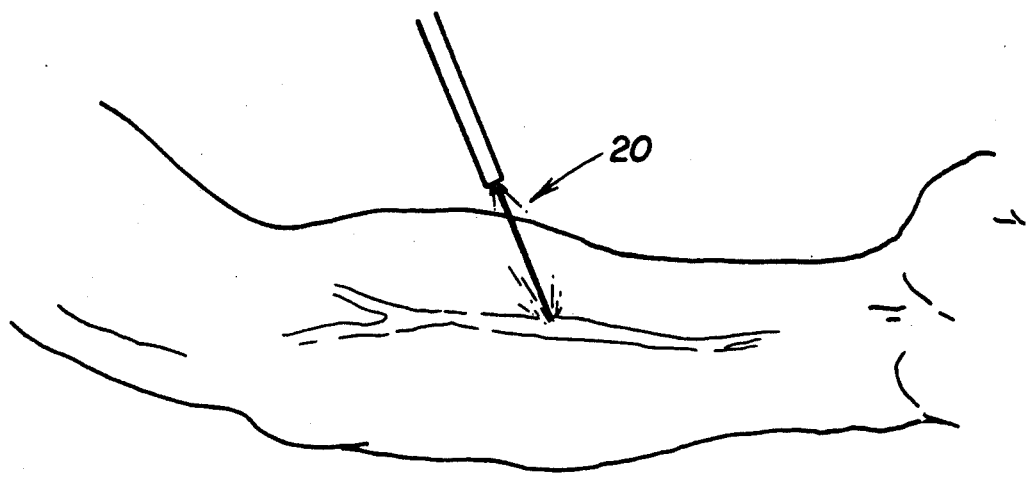
FIG. 4 shows the vein being punctured but with no syringe.
Figure 5:
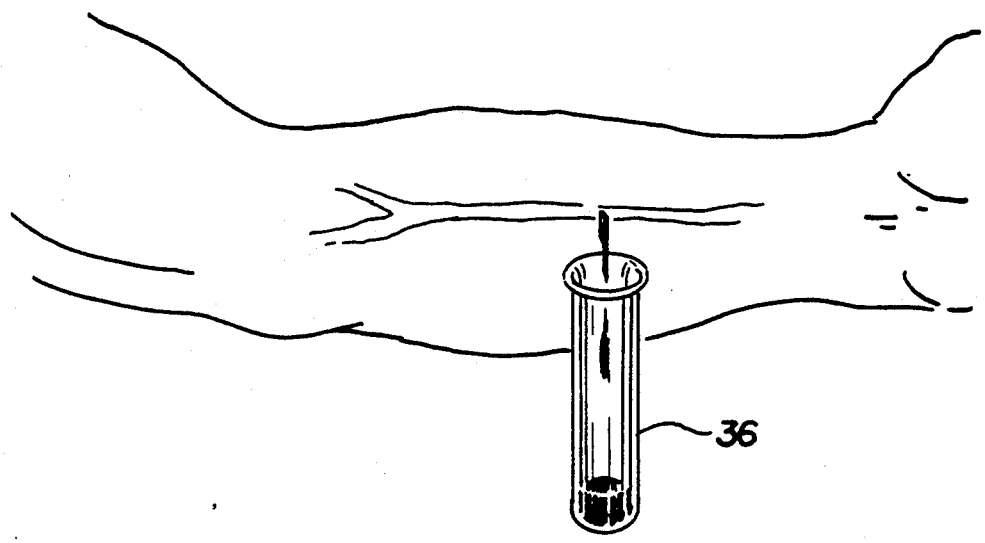
FIG. 5 shows the blood draining out of the hole made as shown in FIG. 4 into a test tube.

Alternately, as shown in FIG. 4, several grams of blood can be collected without the syringe device by merely cleaning the skin on the arm, irradiating a large surface arm vein 24 with laser beam 20, again four 1.5 Joule pulses to produce the same size hole as above. In this case, however, the blood is allowed to drain into test tube 36 as shown in FIG. 5.

While the present invention has been described in connection with a particular embodiment thereof, it will be understood that many changes and modifications of this invention may be made by those skilled in the art without departing from the true spirit and scope thereof. For example, the diameter of the laser beam could be in some cases as low as 0.2 mm or as large as 1.5 mm. Many types of lasers could be used other than the Erbium laser. Lasers chosen should be pulsed or Q-switched and should have preferential absorption by skin tissue or water. Such lasers include carbon dioxide lasers, hydrogen floride lasers, carbon monoxide lasers with frequency doubling as necessary to achieve the proper laser frequency. Persons skilled in the art will recognize that grouped nanosecond pulses could be substituted for single microsecond pulses. The duration of the pulse or series of pulses could be somewhat longer than the recommended 300 us but it should be noted that durations longer than 500 us could result in additional damage to the surrounding tissue and added pain. The upper limit should be about 600 us. If the duration of the pulse or series of pulses is less than amout 100 much of the energy of the beam will be wasted in the form of kinetic energy of the vaporized tissue. Pulse durations of less than 5 us would be extremely inefficient. Accordingly, the appended claims are intended to cover all such changes and modifications as fully within the true spirit and scope of the present invention.

I claim:

1. A blood sampling device for obtaining blood samples through the skin of humans or animals comprising:
   a pulse laser device adjusted to produce a laser pulse having a cross section of about 0.2 to 1.5 mm diameter, with an energy of between 0.5 joules to 4 joules and a duration of between 5 us and 600 us,
   blood sample receptical means for collecting a samples of blood released through holes in skin made by said laser device.

2. A blood sampling device as in claim 1 wherein said laser device is an Erbium laser.

3. A blood sampling device as in claim 1 wherein the duration of the pulse is between 100 us and 300 us.

4. A method of obtaining a blood sample comprising the steps of irradiating human or animal skin with one or more laser pulses of sufficient energy to cause the vaporization of skin tissue so as to produce a hole in the skin extending through the epidermis and to sever at least one blood vessel causing a quantity of blood to be expelled from said hole and collecting at least a portion of said quantity for said sample.

5. The method as in claim 4 wherein said laser pulse is produced by an Erbium laser device.

6. The method as in claim 4 wherein said one or more laser pulses is one pulse having an energy between 0.5 joule and 4 joules and a duration of between 100 us and 300 us and said human or animal skin is the skin of a human finger.

7. The method as in claim 4 wherein said one or more laser pulses is about 4 pulses and said at least a portion of said quantity is collected in a syringe device.

* * * * *

REEXAMINATION CERTIFICATE (3955th)

United States Patent [19]
Tankovich

[11] B1 5,165,418
[45] Certificate Issued Dec. 14, 1999

[54] BLOOD SAMPLING DEVICE AND METHOD USING A LASER

[76] Inventor: Nikola I. Tankovich, 8925 Helen James Ave., San Diego, Calif. 92126

Reexamination Request:
No. 90/004,334, Aug. 15, 1996

Reexamination Certificate for:
Patent No.: 5,165,418
Issued: Nov. 24, 1992
Appl. No.: 07/844,786
Filed: Mar. 2, 1992

[51] Int. Cl.$^6$ .......................................... A61B 5/00

[52] U.S. Cl. ............................... 600/573; 606/16

[58] Field of Search ..................... 128/760, 763, 128/770, 771; 606/13–17, 2, 3, 9, 109, 181, 185

[56] References Cited

PUBLICATIONS

Laser Scarifier Brochure, by Zenit, Nov. 19, 1990 and English translation.

*Primary Examiner*—Max Hindenburg

[57] ABSTRACT

A laser and method for punching tiny holes in human skin for the purpose of taking blood samples. A laser is provided for producing laser pulses in a narrow beam having a cross section of about 0.2 to 1.5 millimeter in diameter to deposit 0.5 joules to 4 joules of laser energy on the skin in a time period of between 5 us and 600 us. A preferred method comprises directing a 1.5 joule, 150 us, 0.5 millimeter diameter pulse at a patient's finger tip. The pulse vaporizes a hole about 1 mm in diameter and 1.5 mm deep to produce about one to three drops of blood for a blood sample. In another preferred embodiment a large vein in the arm is punctured by a four pulse beam of 1.5 joule pulses. A hole of about 1 mm diameter and about 4 mm deep is produced which permits blood samples of several milliliters to be taken.

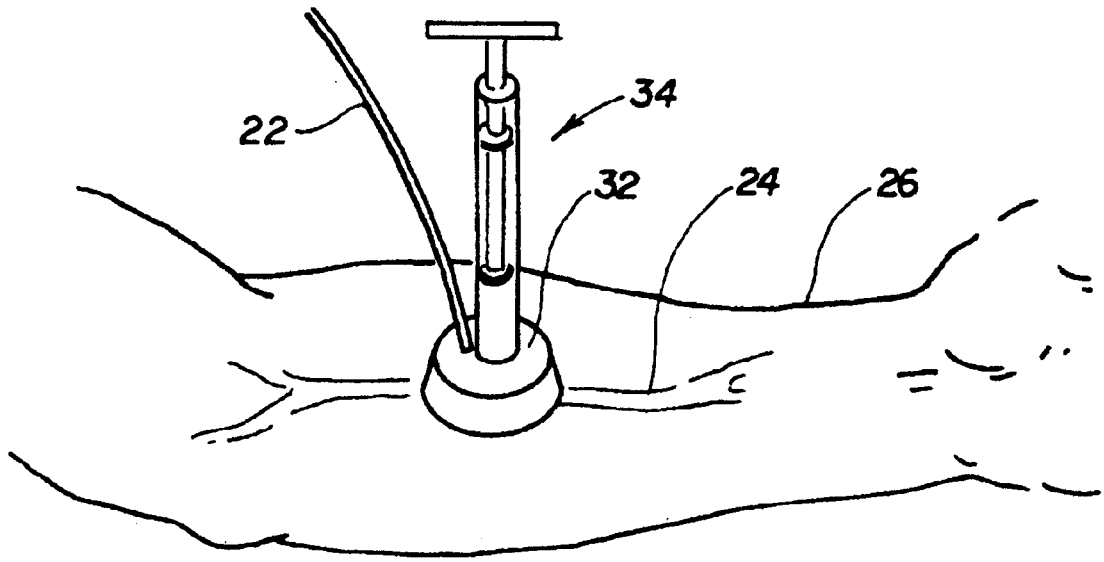

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *